(12) United States Patent
Tulchinsky

(10) Patent No.: US 9,126,925 B1
(45) Date of Patent: Sep. 8, 2015

(54) LIQUID 1,3/1,4-ALKOXYLATED CYCLOHEXANEDIMETHANOL BASED DIACRYLATES

(71) Applicant: Dow Global Technologies LLC, Midland, MI (US)

(72) Inventor: Michael L. Tulchinsky, Midland, MI (US)

(73) Assignee: Dow Global Technologies LLC

( * ) Notice: Subject to any disclaimer, the term of this patent is extended or adjusted under 35 U.S.C. 154(b) by 0 days.

(21) Appl. No.: 14/436,567

(22) PCT Filed: Nov. 1, 2013

(86) PCT No.: PCT/US2013/067985
§ 371 (c)(1),
(2) Date: Apr. 17, 2015

(87) PCT Pub. No.: WO2014/074402
PCT Pub. Date: May 15, 2014

Related U.S. Application Data

(60) Provisional application No. 61/724,094, filed on Nov. 8, 2012.

(51) Int. Cl.
*C07C 67/14* (2006.01)
*C07C 69/602* (2006.01)

(52) U.S. Cl.
CPC .............. *C07C 69/602* (2013.01); *C07C 67/14* (2013.01); *C07C 2101/14* (2013.01)

(58) Field of Classification Search
None
See application file for complete search history.

(56) References Cited

U.S. PATENT DOCUMENTS

| 4,177,315 | A | 12/1979 | Ubersax |
| 4,348,462 | A | 9/1982 | Chung |
| 6,706,779 | B2 | 3/2004 | Bahadur et al. |
| 7,943,725 | B2 | 5/2011 | Baikerikar et al. |
| 2007/0141524 | A1* | 6/2007 | Brennan et al. ................. 433/9 |
| 2010/0048940 | A1 | 2/2010 | Tulchinsky et al. |

OTHER PUBLICATIONS

Brennan, et al., Dental Compositions Containing Radiation-to-Heat Converting Additives for Reducing the Adhesion of the Dental Materials to Tooth, XP002719549, Abstract only.
Baikerikar, et al., UV Curable, Liquid Diacrylate Monomers Based on (cis,trans)-1,3/1,4-cyclohexanedinnethanol, J. Coat. Technol. Res., vol. 7, pp. 175-188, 2010.

* cited by examiner

*Primary Examiner* — Yevegeny Valenrod

(57) ABSTRACT

Disclosed herein are compounds of formula (I): wherein n, $R_1$, and $R_2$ are defined herein. Methods of oligomerizing/polymerizing the compounds of formula (I) and methods of making the compounds of formula (I) are also disclosed.

14 Claims, 2 Drawing Sheets

LIQUID 1,3/1,4-ALKOXYLATED CYCLOHEXANEDIMETHANOL BASED DIACRYLATES

CROSS REFERENCE TO RELATED APPLICATIONS

This application is a 35 USC §371 national phase filing of PCT/US2013/067985 filed Nov. 1, 2013, which claims the benefit of U.S. Application No. 61/724,094, filed Nov. 8, 2012.

FIELD OF THE INVENTION

The instant invention is in the field of monomers and polymers based on a mixture of cis and trans 1,3- and 1,4-alkoxylated cyclohexanedimethanol based diacrylates and methods to produce such mixtures.

BACKGROUND OF THE INVENTION

Radiation cured (typically free radical UV light photopolymerization) coatings and inks are widely used in the coatings and printing industry. Radiation cured coating and ink formulations based cyclohexanedimethanol diacrylates provide excellent end-use properties for the cured coating (such as hardness and strength) but such formulations are difficult to use because the cyclohexanedimethanol diacrylates are solid materials at room temperature and are insoluble in most acrylates. Liquid coating and ink formulations based on ethoxylated or propoxylated cyclohexanedimethanol diacrylates are known but the resulting coating has poorer end use properties.

For example, 1,4-cyclohexanedimethanol has been alkoxylated with either ethylene oxide or propylene oxide and then acrylated to form alkoxylated cyclohexanedimethanol diacrylate based compounds in Scheme 1.

Scheme 1: Chemical structure of alkoxylated cyclohexanedimethanol diacrylates. (Integers m and n in alkoxylated diacrylates are >1 and variable).

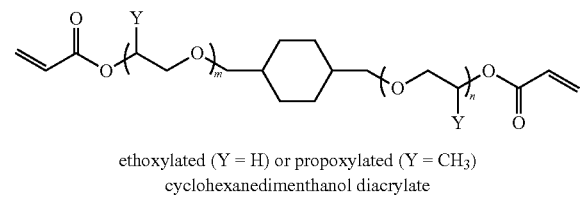

ethoxylated (Y = H) or propoxylated (Y = CH₃)
cyclohexanedimenthanol diacrylate

These products are readily soluble in the acrylates typically used in UV curable formulations and available from Sartomer Company and from Kowa American Corporation as liquids at room temperature. However, the alkoxylation of the 1,4-cyclohexanedimethanol leads to product mixtures with significantly enlarged molecular weights, i.e., m and n are both significantly larger than 1 and represent a statistical mixture. This leads to an undesirable increase in the specific molecular weights of these monomers (ratio of MW to the number of reactive functional groups); thus, the monomer contains a relatively small proportion of functional groups. In addition, the alkoxylation reaction generates useless byproducts such as nonionic, high molecular weight water-soluble poly (ethylene oxide) polymers and 1,4-dioxane. Furthermore, UV cured coatings made from these monomers have inferior properties.

Other related cyclohexanedimethanol based compounds include those disclosed in U.S. Pat. No. 7,943,725, which is owned by The Dow Chemical Company. The U.S. Pat. No. 7,943,725 patent discloses liquid acrylate based compounds of Scheme 2 (below),

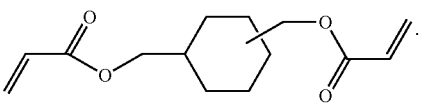

cis/trans 1,3-/1,4-(acryloxymethyl)cyclohexane

These diacrylate compounds exist as a mixture containing the 1,3- and 1,4-isomers in an approximately 1-to-1 ratio. A disadvantage of this mixture is that it is a mixture of predominantly solid (but also some liquid) at room temperature, whereas liquid compounds are preferred. In order to generate the desired mixture of liquid diacrylates, it is necessary to either reduce the amount of the trans-1,4-cyclohexanedimethanol isomer in the starting diol to below 15% or purify the diacrylate reaction mixture by reducing the trans-1,4-diacrylate content to below 15%. These purifications are time consuming and lead to increased costs associated with the preparation of the monomer mixture.

It would be advantageous if liquid cyclohexanedimethanol diacrylate based coatings and ink formulations having improved properties, and that 1) did not create a statistical mixture of products, 2) reduced the formation of by-products, and 3) did not require a separate purification step to remove the trans-1,4-cyclohexanedimethanol isomer, could be prepared.

SUMMARY OF THE INVENTION

Disclosed herein are mixtures of alkoxylated cyclohexanedimethanol based diacrylates, dimethacrylates, dicrotonates, and ditiglates that are liquid at room temperature and which can be used to make coatings having excellent hardness, strength, clarity, abrasion resistance, adhesion, stain resistance and solvent resistance properties. These compounds do not exist as a statistical mixture or products (as is the case for the compounds of FIG. 1), and they do not require the removal of at least some of the trans-1,4-cyclohexanedimethanol isomer in order to generate a liquid product (as is the case for the U.S. Pat. No. 7,943,725 patent).

In one aspect, disclosed herein is a mixture of compounds useful to make a polymer or a prepolymer, the mixture of compounds comprising compounds of formula I:

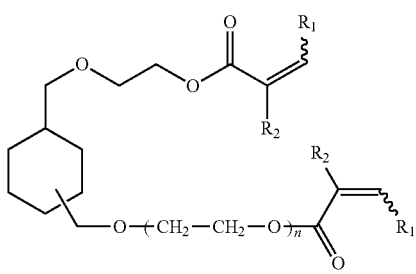

wherein
n is 0 or 1;
$R_1$ is H or methyl; and
$R_2$ is H or methyl.

In another aspect, disclosed herein are polymers and/or prepolymers comprising units of formula II:

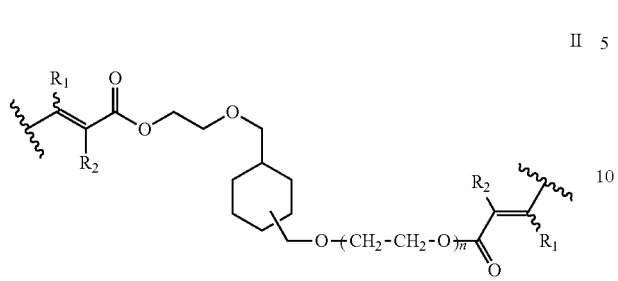

(II)

wherein
n is 0 or 1;
$R_1$ is H or methyl; and
$R_2$ is H or methyl.

In yet another aspect, disclosed herein are methods of making compounds of formula (I):

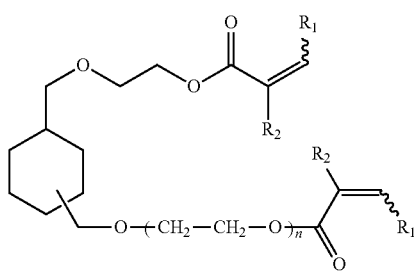

(I)

wherein n is 0 or 1;
$R_1$ is H or methyl; and
$R_2$ is H or methyl;
the method comprising reacting diols of formula (III)

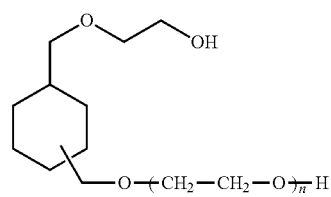

(III)

with i) an ester of formula (V), optionally in the presence of an acid or base catalyst;

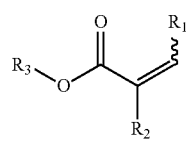

(V)

wherein
$R_3$ is $C_1$-$C_3$ alkyl;
$R_1$ is H or methyl;
$R_2$ is H or methyl; or ii) an acylating agent, of the formula:

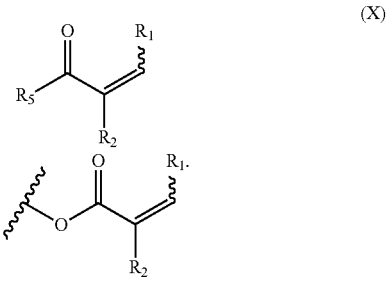

(X)

wherein $R_5$ is Cl, OH, or

DETAILED DESCRIPTION

Figure 1:
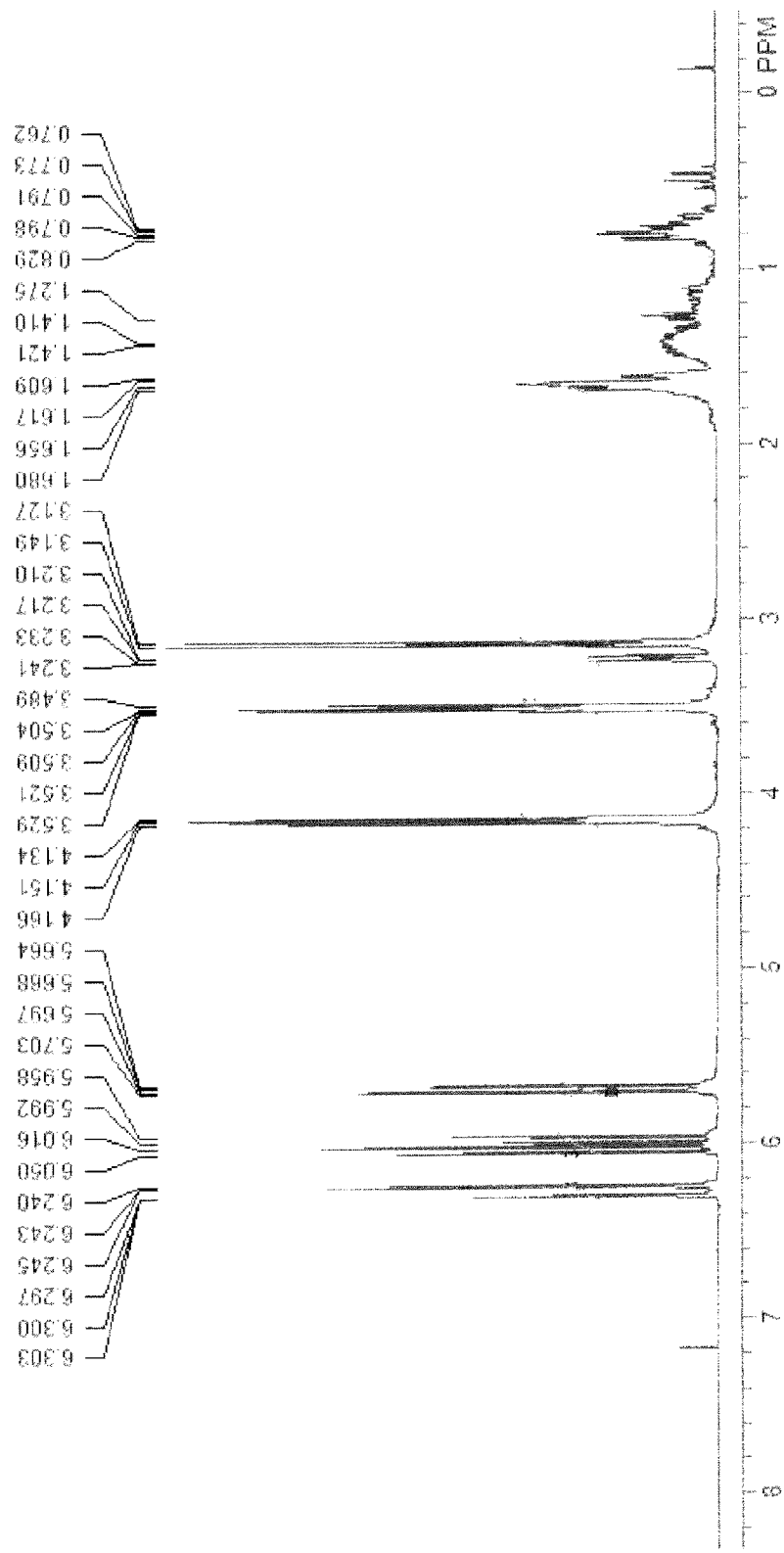
FIG. 1 is the $^1$H NMR in $CDCl_3$ of the mixture of the four isomers (cis-1,4; trans-1,4; cis-1,3; trans-1,3) of the diacrylated, bis-etherified product made in Example 1 (below).

As mentioned above, described herein are mixtures of compounds of formula I. Such mixtures exist as a combination of 1,3- and 1,4-isomers and further exist in both the cis and/or trans configurations. An advantage of such mixtures is that they do not require a separate purification step in order to be a liquid at room temperature. But if desired the mixtures described herein may be purified using methods known in the art, such as distillation or column chromatography.

In another embodiment, preferred compounds of formula I comprise compounds of formula Ia:

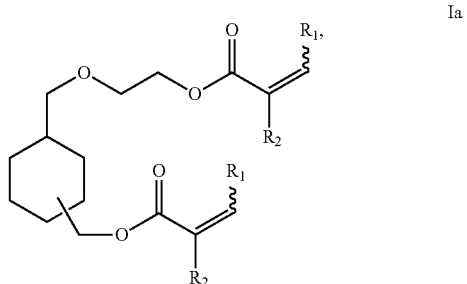

Ia where $R_1$ and $R_2$ are as defined above.

In one embodiment, preferred compounds of formula I comprise compounds of formula Ib:

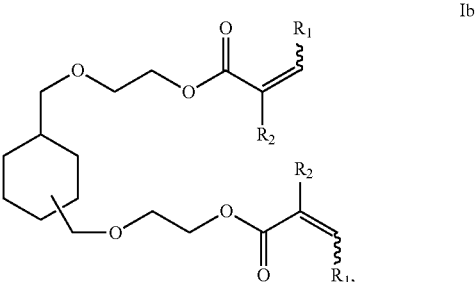

Ib where $R_1$ and $R_2$ are as defined above.

The compounds of formula Ib are more preferred than the compounds of formula Ia.

In one embodiment, in compounds of formulas Ia and Ib, at least one of $R_1$ and $R_2$ is methyl. In another embodiment, both $R_1$ and $R_2$ are methyl. In still another embodiment, $R_1$ and $R_2$ are H.

In another aspect, disclosed herein are methods of preparing the compounds of formula (I):

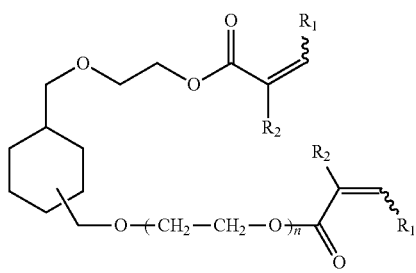
(I)

wherein n is 0 or 1;
$R_1$ is H or methyl; and
$R_2$ is H or methyl;
the method comprising reacting diols of formula (III)

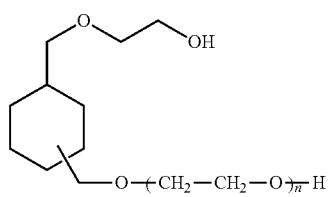
(III)

with
i) an ester of formula (V), optionally in the presence of an acid or base catalyst;

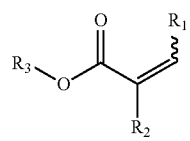
(V)

wherein
$R_3$ is $C_1$-$C_3$ alkyl;
$R_1$ is H or methyl;
$R_2$ is H or methyl; or
ii) an acylating agent, of the formula:

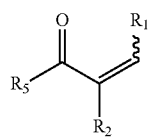
(X)

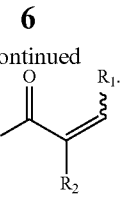

wherein $R_5$ is Cl, OH, or

When the diol of formula II is reacted with the acylating reagent of formula X, it is preferred that $R_5$ is Cl or

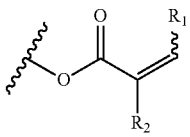

and the acylation reaction is performed in the presence of a base. Suitable bases are known in the art and include amine containing bases, NaOH, KOH, and LiOH, with the amine containing bases being preferred. Examples of amine containing bases include triethylamine, diisopropylethylamine, pyridine, lutidine, dimethylaminopyridine, 2,6-di-tertiary butyl pyridine, 1,8-bis(dimethylamino)naphthalene, and/or combinations thereof. Preferred amines include triethylamine, diisopropylethylamine, pyridine, lutidine, dimethylaminopyridine, or combinations thereof. Most preferred bases include triethylamine, diisopropylethylamine and combinations thereof.

When an acylating agent of formula X is used, the acylation reaction is commonly performed in a solvent. Suitable solvents are those that do not react with the acylating agent or otherwise impede the acylation reaction. Examples of suitable solvents include toluene, xylene, benzene, tetrahydrofuran, dibutyl ether, diethyl ether, methylene chloride, chloroform, dichloroethane, or combinations thereof. Preferred solvents include toluene, tetrahydrofuran, dibutyl ether, diethyl ether, methylene chloride, or combinations thereof.

Typically, the acylation reactions performed using acylation reagent of formula X are run at a temperature of −20 to 35° C. More preferably, they are run at a temperature of −10° C. to 30° C. Still more preferably, they are run at a temperature of −10° C. to 15° C. Even more preferably, they are run at a temperature of −5° C. to 5° C.

In one preferred embodiment, in the acylating agent of formula X, $R_5$ is Cl.

In another preferred embodiment, in the acylating agent of formula X, $R_5$ is

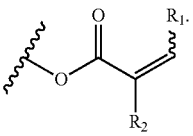

In such an embodiment, which is directed towards the use of the anhydride, it is further preferred that all occurrences of $R_1$ carry the same definition and that all occurrences of $R_2$ carry the same definition. But the definitions of $R_1$ and $R_2$ may be different.

In further embodiments, i) both $R_1$ and $R_2$ are H or ii) only one of $R_1$ and $R_2$ is H. In a preferred embodiment, both $R_1$ and $R_2$ are H.

In still another embodiment, at least one of $R_1$ and $R_2$ is methyl. In another embodiment, both $R_1$ and $R_2$ are methyl.

In yet another embodiment, one of $R_1$ and $R_2$ is methyl, while the other is H.

Alternatively, $R_5$ may be OH. In such cases, an acid catalyst is used to accelerate the rate of the esterification reaction. Typically, the water that is formed during the esterification reaction is removed using a Dean-Stark apparatus or at least one dehydrating agent. As a general rule, solvents are not used in this reaction. The stoichiometric ratio of the reagents may be ascertained by one of skill in the art. Preferred catalysts for this reaction are acid catalysts, which include mineral acids and organic acids. Examples of acceptable acids include HCl, $H_2SO4$, $H_3PO_4$, p-toluene sulfonic acid, triflic acid, and methane sulfonic acid. Typically, the reaction is run at temperatures from 20° C. up to and including the reflux temperature of the reaction mixture.

In alternate embodiments, the acylation reaction is a transesterification reaction performed using the ester of formula (V), optionally in the presence of an acid or base catalyst. Any acid or bases catalyst known in the art to catalyze the transesterification reaction may be used. Examples of acid catalysts include HCl, $H_2SO_4$, $H_3PO_4$, p-toluene sulfonic acid, triflic acid, and methane sulfonic acid. Examples of bases catalysts include LiOH, NaOH, KOH, and $Ca(OH)_2$.

In such reactions, the ester of formula (V) is used as the solvent.

The most appropriate reaction temperature for the transesterification may be readily ascertained by one of skill in the art. Typical temperatures include 0 to 30° C. More typically, the reaction is run at temperatures of 15-25° C.

In one embodiment, i) both $R_1$ and $R_2$ are H or ii) only one of $R_1$ and $R_2$ is H. In a preferred embodiment, both $R_1$ and $R_2$ are H.

In an alternate embodiment at least one of $R_1$ and $R_2$ is methyl. In another embodiment, both $R_1$ and $R_2$ are methyl.

In yet another embodiment, one of $R_1$ and $R_2$ is methyl, while the other is H.

Preferably, in the ester of formula (V), $R_3$ is $CH_3$.

In one embodiment, the compounds of formula (I) are prepared by reacting dialdehydes of formula (IV)

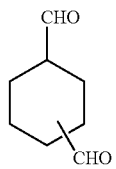
(IV)

with ethylene glycol and hydrogen, in the presence of a catalyst. A preferred catalyst is Pd/C.

The preferred compounds of formula I made using the above methods are:

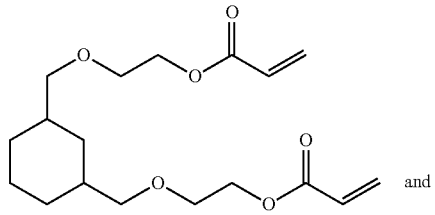
and

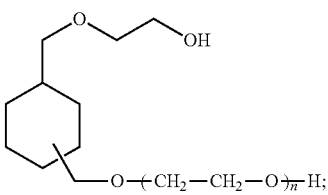

In a preferred embodiment, methods of preparing compounds of formula (I)

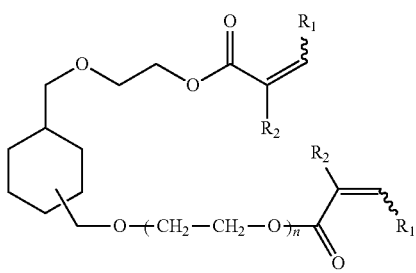

where
n is 0 or 1;
$R_1$ is H or methyl; and
$R_2$ is H or methyl
comprise
reacting dialdehydes of formula (IV)

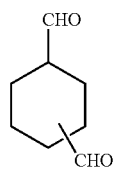
(IV)

with hydrogen and at least 7 and up to and including 100 equivalents of ethylene glycol, in the presence of a Pd/C catalyst to form compounds of formula (II)

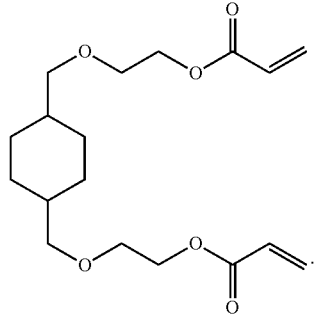
(III)

acylating compounds of formula III with an acylating agent, in the presence of a base and a solvent, wherein the base is selected from the group consisting of triethylamine, di(isopropyl)ethylamine and combinations thereof, and the solvent is selected from the group consisting of toluene, tetrahydrofuran, dibutyl ether, diethyl ether, methylene chloride, and combinations thereof, wherein the acylating agent has the formula:

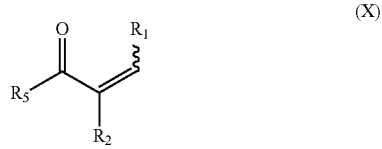

wherein $R_5$ is Cl; and
either both $R_1$ and $R_2$ are H or only one of $R_1$ and $R_2$ is H; and
wherein the acylation reaction is run at a temperature of −10° C. to 20° C.

In a further preferred embodiment, the reaction between dialdehydes of formula (IV) and the ethylene glycol occurs at a temperature greater than or equal to 100° C. and up to and including 250° C. and at a pressure of at least 50 pounds per square inch up to and including 1200 pounds per square inch.

Schemes

The following schemes illustrate one possible method of making the claimed compounds. In the first step, the dialdehyde, which comprises the 1,3- and 1,4-isomers and also both the cist and trans isomers, is reductively etherified using an excess of diol (with ethylene glycol being preferred, although other diols may be used) in the presence of hydrogen gas, and a catalyst, at a pressure higher than ambient pressure and a temperature above room temperature. See U.S. Publication No. 2010/0048940 for more information on the reductive etherification reaction. One preferred method of conducting the reductive etherification reaction is to use at least 7 equivalents of diol, $H_2$ gas at a pressure of 1000 psi, 5% Pd/C, at a temperature of 200° C. and a reaction time of four hours.

The resulting product then comprises the bis-etherified product (major product, approximately 95%), and a mono-etherified product (minor product, approximately 5%), which is formed when one of the aldehydes undergoes reductive etherification, while the other aldehyde group is reduced to the alcohol under the reductive etherification conditions.

Scheme 1

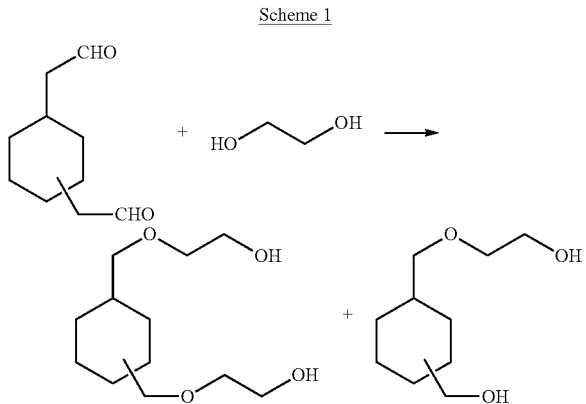

This mixture of mono- and bis-etherified products may be separated using methods known in the art, such as distillation and/or column chromatography. More specific examples of purification methods that may be used include vacuum distillation at 144-149° C. at 0.25 mm Hg or silica gel column chromatography with 5:1 hexanes:ethyl acetate.

The second step involves the acylation of the alcohol groups, using an acylating agent/protocol as described herein.

Scheme 2: Acylation of the bis-etherified product:

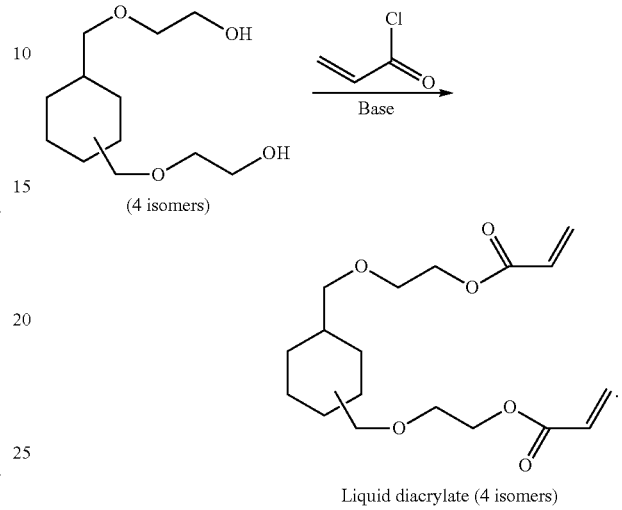

Scheme 3

Acylation of the Mono-Etherified Product

Scheme 3: Acylation of the mono-etherified product:

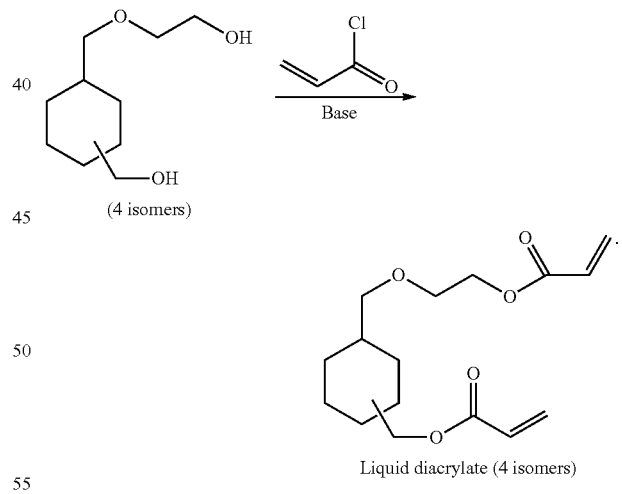

In both of the above acylation reactions, the acylating reagent is acryloyl chloride. As mentioned above, other acylating agents or acylating protocols may be used to make the bis-acylated materials. Likewise, as described above, the base may be any of a variety of bases that are known in the art to be useful in the preparation of acrylated products. Or (as described above), the acylating reaction may instead be a transesterification reaction.

If desired, the bis-acylated, mono-etherified product may be selectively made using a mono-protected aldehyde as a starting material, mono-etherifying the unprotected aldehyde, deprotecting the protected aldehyde group, reducing the aldehyde to an alcohol, and then acylating the two alcohol groups. Acceptable protecting agents and reaction conditions are known in the art and/or may be determined by the disclosure contained herein.

The monomers and prepolymers of the instant invention can be blended with a filler, preferably inorganic nanoparticles such as colloidal silica to prepare colloidal silica preparations (such as a colloidal silica acrylate system). Colloidal silica acrylates provide, for example and without limitation, enhanced scratch resistance to acrylate coatings. Colloidal silica acrylates are disclosed in, for example and without limitation, U.S. Pat. Nos. 4,177,315 and 4,348,462.

The monomers and prepolymers described herein are typically polymerized by free radical polymerization techniques such as by the use of a peroxide polymerization catalyst. However, such monomers and prepolymers of the instant intention are most preferably polymerized by free radical photopolymerization techniques using a photoinitiator activated by UV light. For applications in which the formulation is; cured by electron beam (EB) radiation, a photoinitiator is not required to initiate polymerization.

The resulting oligomerized/polymerized compounds comprise compounds of formula (II).

EXAMPLES

Example 1

Acylation of the Bis-Etherified Product

A mixture of 1,3- and 1,4-bis(4-hydroxy-2-oxabutyl)cyclohexane (Scheme 2) was prepared earlier according to the teachings of US 20100048940.

1,3-/1,4-bis(4-hydroxy-2-oxabutyl)cyclohexane (11.6 g; 50 mmol, MW=232.3) is mixed with toluene (40 ml) and di(isopropyl)ethylamine (18.1 g; 140 mmol) and cooled to 0° C. using an ice bath. Acryloyl chloride (11.25 g; 125 mmol) in toluene (20 ml) is slowly added over ~30 min with stirring. After the addition is done, the mixture is stirred for one more hour and then warmed to room temperature. The mixture is filtered, and the solid residue is washed with toluene (20 ml). The combined filtrate is washed with water saturated with NaCl (2×20 ml) and then dried over $MgSO_4$. Toluene is removed using a rotovap, and the residue is additionally dried in high vacuum for about 2 hours. The resulting crude product is chromatographed on silica gel using hexane-ethyl acetate (from 40:1 to 10:1). The fractions containing 95% material or more are combined, polymerization inhibitor MEHQ (hydroquinone monomethyl ether) (100 ppm) in hexanes is added, the solvent is evaporated, and the residue is additionally dried in high vacuum to a constant weight. The pure material (~95% purity) is characterized by $^1H$ and $^{13}C$ NMR.

$^1H$ NMR spectrum ($CDCl_3$, δ, ppm): 1.1-1.8 m (10H, cyclohexyl); 3.14 d (4H), 3.51 m (4H), 4.15 m (4H) $CH_2O$— groups; 5.68 m (2H), 6.00 m (2H), 6.25 m (2H) acrylate, ABX-pattern.

Figure 2:
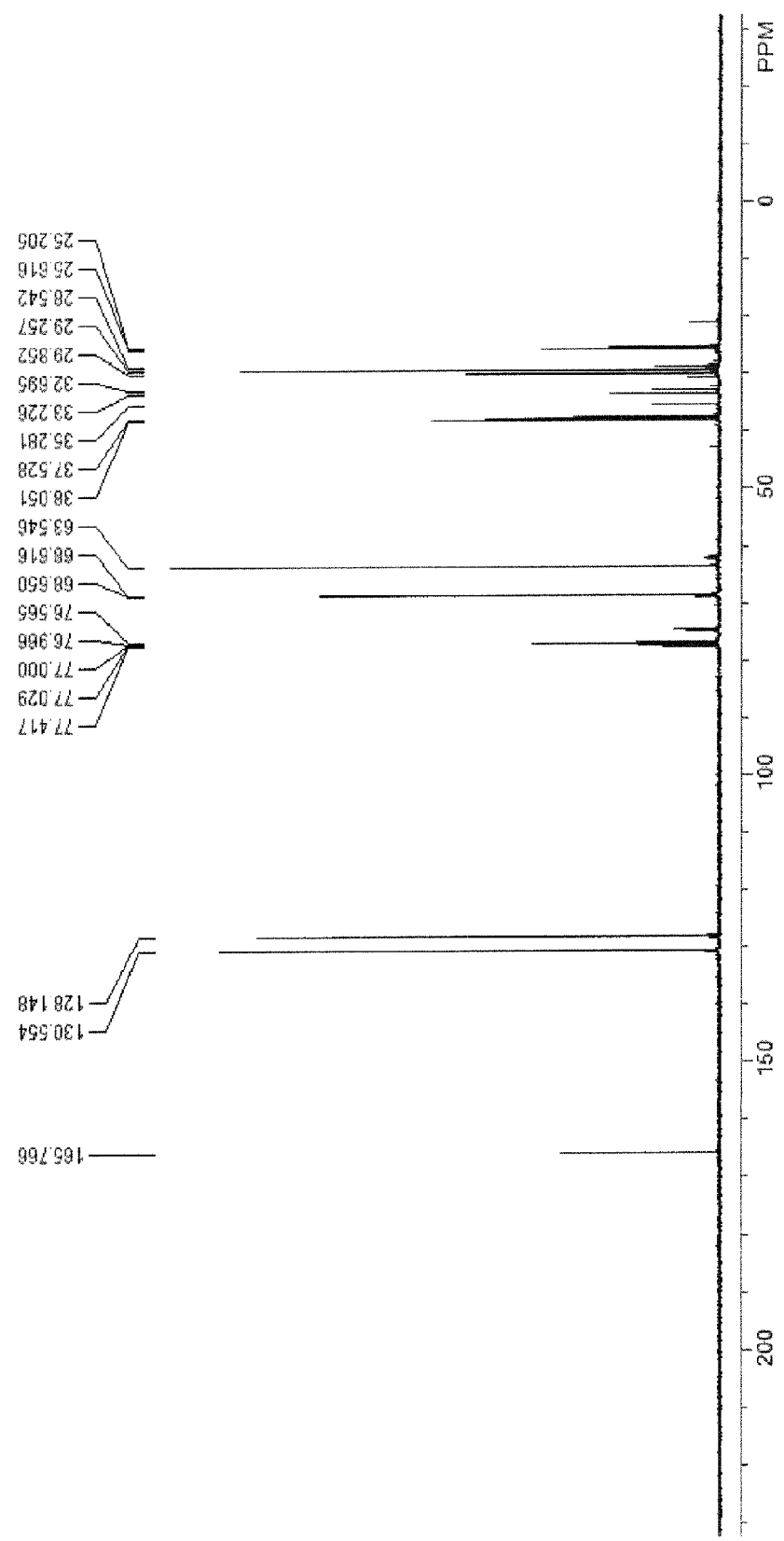
FIG. 2 is the $^{13}$C NMR in $CDCl_3$ of the mixture of the four isomers (cis-1,4; trans-1,4; cis-1,3; trans-1,3) of the diacrylated, bis-etherified product made in Example 1 (below).

$^{13}C$ NMR spectrum ($CDCl_3$, δ, ppm): 25.21; 25.62; 28.54; 29.26; 29.85; 32.70; 33.23; 35.28; 37.53; 38.05; 63.55; 68.62; 76.57; 76.97; 128.15; 130.55; 165.766. See FIGS. 1 and 2 for the corresponding NMR spectra.

Example 2

Physical State of Example 1 at Both Room Temperature and at +5° C.

The liquid sample prepared in Example 1 was kept at room temperature for one week. The material remained a liquid and did not show any sign of solidifying.

The sample was also placed in the refrigerator at +5° C. for one week. The material did not solidify.

What is claimed is:

1. Compound of formula (I):

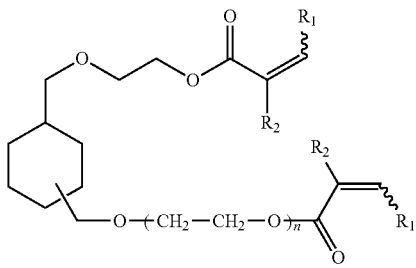

wherein
n is 0 or 1;
$R_1$ is H or methyl; and
$R_2$ is H or methyl.

2. Compound according to claim 1 of the formula:

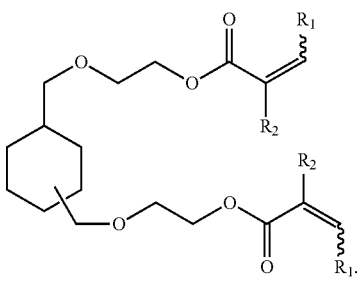

or of the formula:

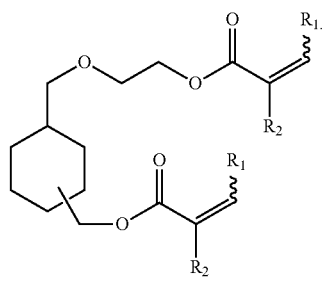

3. Method of preparing the compound of formula (I):

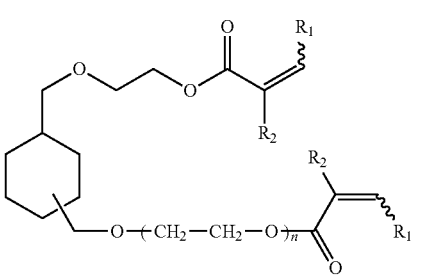

(I)

wherein n is 0 or 1;

$R_1$ is H or methyl; and
$R_2$ is H or methyl;
the method comprising reacting diol of formula (III)

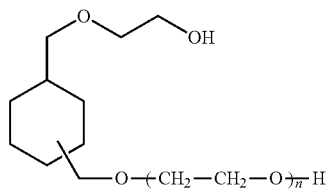

with i) an ester of formula (V), optionally in the presence of an acid or base catalyst;

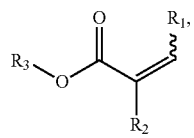

wherein
$R_3$ is $C_1$-$C_3$ alkyl;
$R_1$ is H or methyl;
$R_2$ is H or methyl; or
ii) an acylating agent, of the formula:

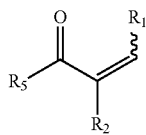

wherein $R_5$ is Cl, OH, or

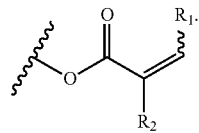

4. Method according to claim 3, wherein $R_5$ is Cl and the acylation reaction is performed in the presence of a base.

5. Method according to claim 3, wherein the base is triethylamine, diisopropylethylamine, pyridine, lutidine, dimethylaminopyridine, or combinations thereof.

6. Method according to claim 3, wherein, $R_5$ is Cl or

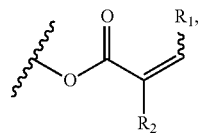

and either i) both $R_1$ and $R_2$ are H or ii) only one of $R_1$ and $R_2$ is H.

7. Method according to claim 3, wherein the acylation reaction with a compound of formula (X) is performed at a temperature of −10° C. to 30° C.

8. Method according to claim 3, wherein the acylation reaction is performed in the presence of a solvent, wherein the solvent comprises toluene, tetrahydrofuran, dibutyl ether, diethyl ether, methylene chloride, or combinations thereof.

9. Method according to claim 3, wherein, in the ester of formula (V), $R_3$ is $CH_3$.

10. Method according to claim 3, wherein compound of formula (III) are prepared by reacting dialdehyde of formula (III)

with ethylene glycol and hydrogen, in the presence of a catalyst.

11. Method according to claim 10, wherein the catalyst is Pd/C.

12. Method according to claim 3, wherein the compound of formula (I) are

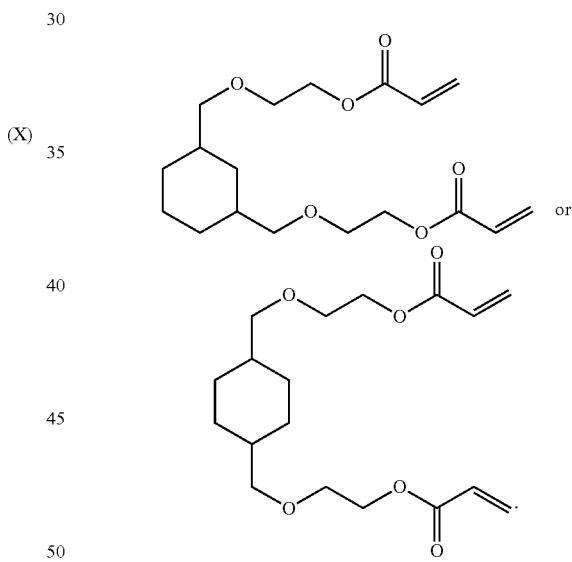

13. Method according to claim 3, of preparing compound of formula (I)

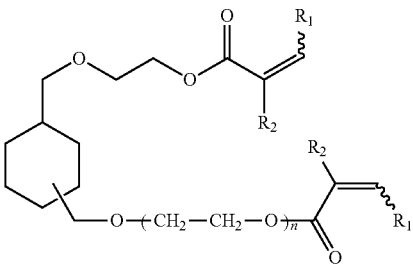

where
n is 0 or 1;
$R_1$ is H or methyl; and
$R_2$ is H or methyl
comprising
reacting dialdehyde of formula (III)

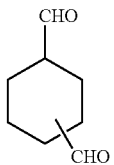

(IV)

with hydrogen and at least 7 and up to and including 100 equivalents of ethylene glycol, in the presence of a Pd/C catalyst to form compound of formula (III)

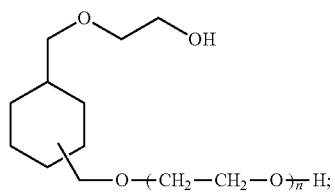

(III)

acylating compound of formula (III) with an acylating agent, in the presence of a base and a solvent, wherein the base is selected from the group consisting of triethylamine, di(isopropyl)ethylamine and combinations thereof, and the solvent is selected from the group consisting of toluene, tetrahydrofuran, dibutyl ether, diethyl ether, methylene chloride, and combinations thereof, wherein the acylating agent has the formula:

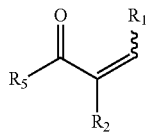

(X)

wherein $R_5$ is Cl; and
either both $R_1$ and $R_2$ are H or only one of $R_1$ and $R_2$ is H; and
wherein the acylation reaction is run at a temperature of −10° C. to 20° C.

14. Method according to claim 13, wherein the reaction between dialdehyde of formula (IV) and the ethylene glycol occurs at a temperature greater than or equal to 100° C. and up to and including 250° C. and at a pressure of at least 50 pounds per square inch up to and including 1200 pounds per square inch.

* * * * *